United States Patent [19]

Sickenberger et al.

[11] Patent Number: 5,517,026
[45] Date of Patent: May 14, 1996

[54] ON-THE-MOVE SURFACE SAMPLING HEAD FOR A MASS SPECTROMETER

[75] Inventors: David Sickenberger, Bel Air; Emory Sarver, Havre de Grace, both of Md.

[73] Assignee: The United States of America as represented by the Secretary of the Army, Washington, D.C.

[21] Appl. No.: 376,169

[22] Filed: Jan. 20, 1995

[51] Int. Cl.⁶ .................................................. H01J 45/00
[52] U.S. Cl. ........................................... 250/288; 250/281
[58] Field of Search .................................. 250/281, 288, 250/288 A

[56] References Cited

U.S. PATENT DOCUMENTS

| | | |
|---|---|---|
| 3,681,598 | 8/1972 | Thurston ................................ 250/288 |
| 5,123,274 | 6/1992 | Carroll et al. . |
| 5,416,321 | 5/1995 | Sebastian et al. ..................... 250/288 |

FOREIGN PATENT DOCUMENTS 0101845  8/1980  Japan ...................................... 250/288

OTHER PUBLICATIONS

Department of the Army Technical Manual, Draft Operator's Manual, TM 3–6665–339–10, pp. 1–34, Feb. 1994.
Bruker–Franzen User Manual, MM–1 User Manual, pp. 2–4, 2–5 Dec. 1991.
Josef Reithmeier, "The FUCHS, and NBC Reconnaissance Specialist" Military Technology, Special Supplement, ISSN 0722–3226, pp. 24–26 has no date.

*Primary Examiner*—Jack I. Berman
*Assistant Examiner*—Kiet T. Nguyen
*Attorney, Agent, or Firm*—Edward L. Stolarun; Michael C. Sachs

[57] ABSTRACT

An on-the-move surface sampling head utilizes a silicone membrane with an internal neater in conjunction with a mass spectrometer analyzer and a modified transfer line having a quick-connect electrical-pneumatic connector to detect chemical contaminated areas.

16 Claims, 2 Drawing Sheets

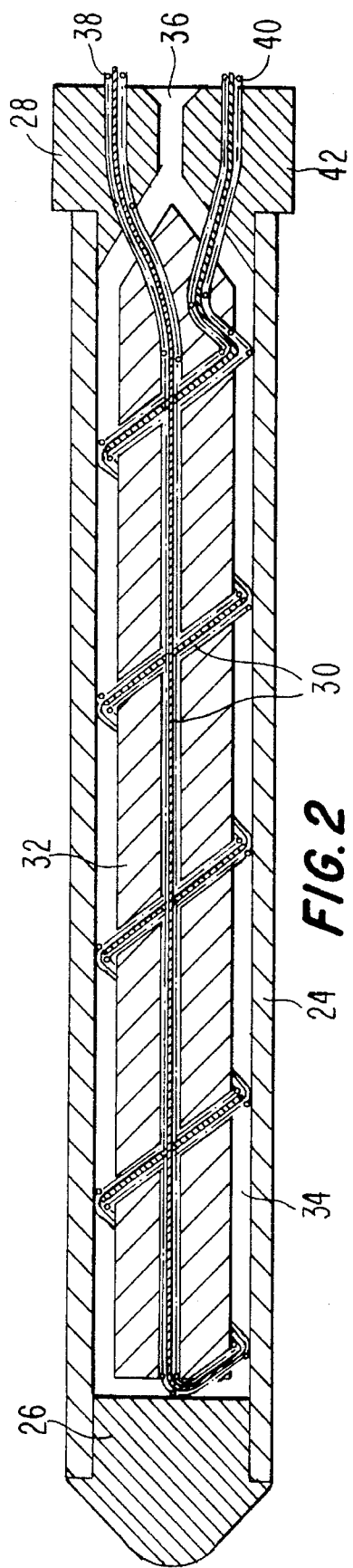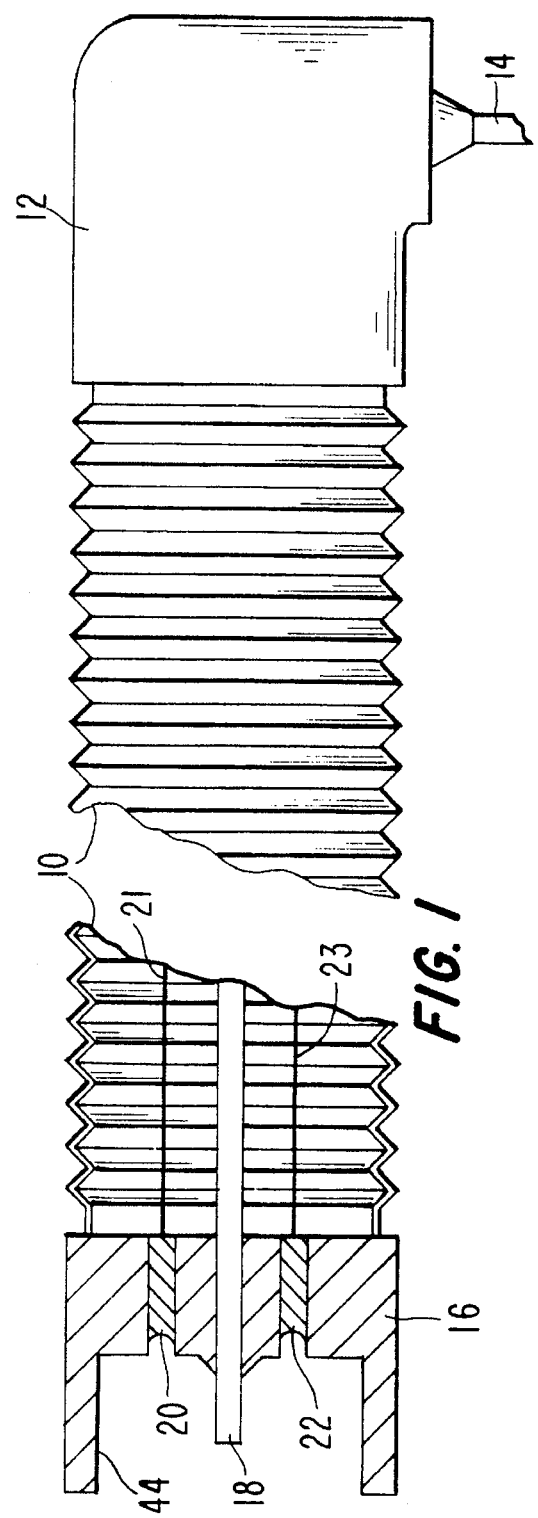

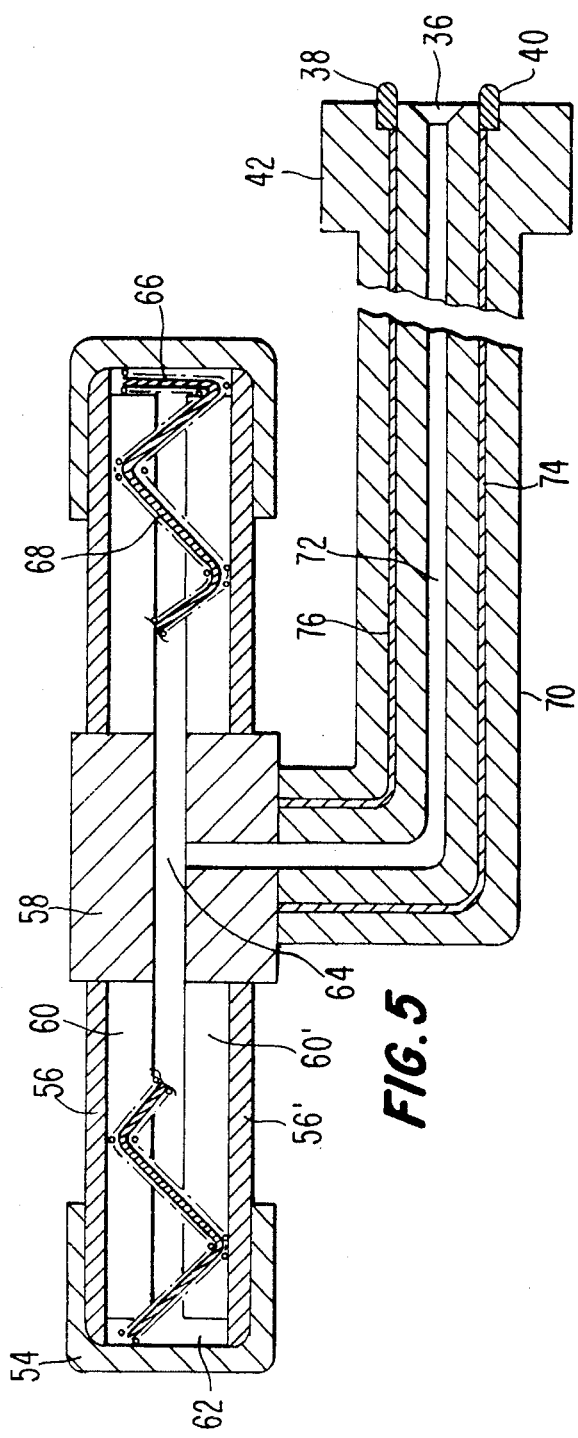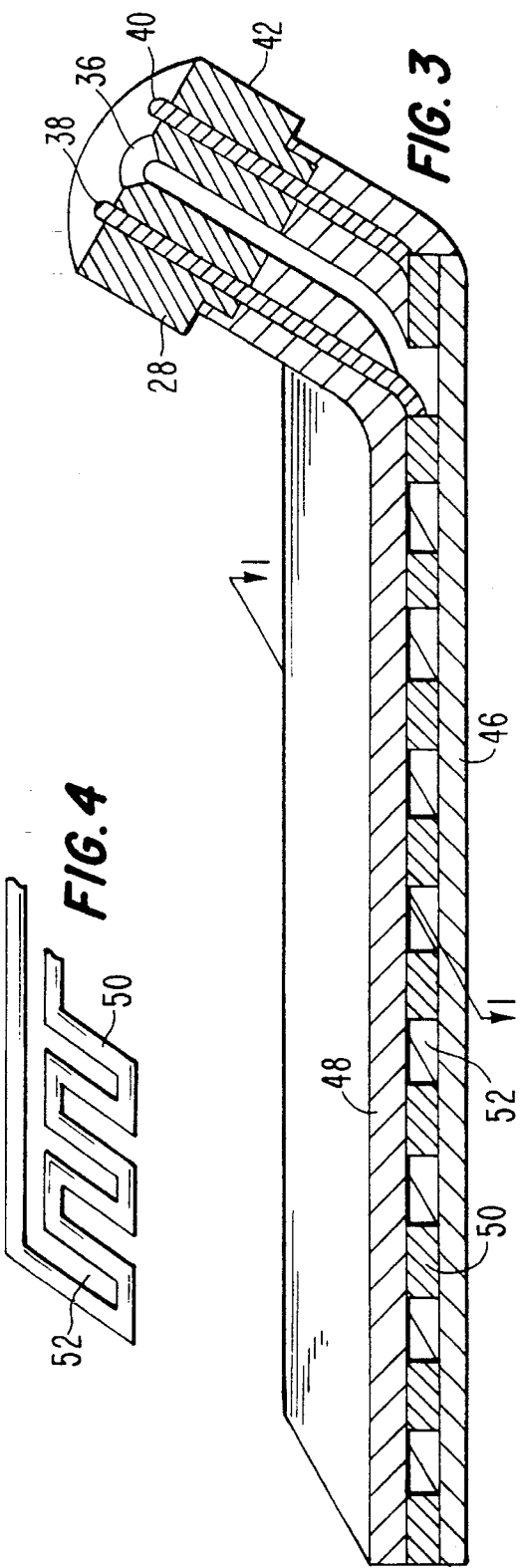

ON-THE-MOVE SURFACE SAMPLING HEAD FOR A MASS SPECTROMETER

CROSS REFERENCE TO RELATED APPLICATIONS

This application is a substitute application for abandoned application Ser. No. 07/775,390, filed on Oct. 15,1991.

BACKGROUND OF THE INVENTION

The present invention relates to an on-the-move surface sampling probe used in conjunction with a mass spectrometer for the purpose of detecting chemical contaminated areas. Under present day conditions, considering the proliferation of chemical weapons, it is extremely important for combat forces to be able to mark and identify chemical areas of contamination, identify clear lanes of passage, and report this information to appropriate command elements.

In the past there has been no stand-alone chemical agent detector that could directly analyze ground surfaces for residual chemical agent contamination while being operated from a moving platform.

Prior art chemical agent detectors, one of which is known as the GErman Mass Spectrometer (GEMS) utilizes a gas chromatograh/quadrupole mass analyzer consisting of a heated sampling probe and mass analyzer assembly. The prior art probe comprised a heated sampling head and a 3.5 meter transfer column. In these prior art devices a liquid or solid sample is introduced into the sampling head by placing the sample in contact with a neared silicone coated wire membrane located at the end of the probe. The heated membrane vaporizes the chemical agent on contact which then passes through the membrane into the column and then to the mass spectrometer where the contaminating substance is analyzed. The problem with these prior art GEMS probes was that they could not be placed directly onto the ground from a moving platform, because contact with road and surface obstacles would damage the probe making it non-functional.

As a result of the aforementioned problems the prior art probes nave been modified to integrate the GEMS heated sampling probe with ground sampling devices. These ground sampling devices provide the means by which surface contamination can be brought from the ground to a GEMS probe while the vehicle is moving. These sampling devices act as transfer mechanism to pick up the contaminating agent, off the ground and deliver it to the GEMS probe. These prior art sampling devices generally consist of two independent booms which can be raised or lowered from within the vehicle either manually or automatically. Each boom contains some form of silicone rubber sampling element, such as a wheel. In the lowered position, the sampling element contacts the ground and rolls or drags freely. Periodically it is necessary to raise one of the booms while the other one is lowered. The element on the raised boom is then contacted to the GEMS' probe. If the sampling element is found to be clean, the boom and element are lowered and the second boom is raised and analyzed. This process is repeated until contamination is discovered. The contaminated sampling element has to be replaced with a clean element. A catcher or alignment device is required to insure that the sampled element is correctly positioned for the GEMS probe.

The problem with the aforementioned prior art device is that since both sampling booms share the same GEMS probe head, the alignment of the boom with the sampling head is critical. Testing of these prior art devices indicates that normal NBC Reconnaissance Systems movement alter the alignment to the point that the sampling system fails to operate. Another problem with the dual boom prior art device is the complexity required in the mechanical and electrical control circuits which must be used to properly time booms position. This complexity results in increased hardware costs, lack of reliability and more training time. A further problem with these prior art devices is the GEMS probe must be heated to maintain a rapid response to the sampled element. This design results in a mud build up on the probe and can result in the failure of the system to operate. Alignment devices used in the prior art design present an additional problem of cross contamination. A new sampling element may become contaminated by the catcher, thus giving misleading indications.

SUMMARY OF THE DISCLOSURE

The present invention relates to a transfer line and an on-the-move surface sampling probe to allow a GEMS to analyze ground surfaces for contamination.

An object of the present invention is to incorporate a modified transfer line with an on-the-move ground sampling head for use with a chemical agent detector (GEM) which eliminates the need of clean-up tools and decontamination procedures.

Another object of the present invention is to eliminate the need of a separate surface sampling device, such as dual booms and catcher assemblies, for sampling contaminated NBC areas.

Another object of the present invention is to provide for an on-the-move surface sampling probe for a chemical agent detector which requires no control electronics to regulate the sampling operation.

Another object of the present invention is to provide for a transfer line and an on-the-move sampling head for a GEMS which can easily be replaced through a quick-connect connection between modified transfer line and an on-the-move sampling head.

Another object of the present invention is to eliminate the need for catcher or alignment devices, used with a sampling probe of a GEMS, which have the potential of cross contamination.

A further object of the present invention is to provide for an improved transfer line and on-the-move ground sampling head for a GEMS which allows for larger and more efficient sampling surfaces.

For a better understanding of the present invention, together with other and further objects, thereof, reference is made to the following descriptions taken in connection with the accompanying drawings.

BRIEF DESCRIPTION OF THE DRAWINGS

FIG. 1 is a partial cut away longitudinal cross-sectional view of the transfer 1 line.

FIG. 2 is a diametral longitudinal cross-sectional view of a tube sampling head.

FIG. 3 is a partial longitudinal cross-sectional view of an on-the-move bar type sampling head.

FIG. 4 is a partial plan view of the neater element taken along line 1—1 of FIG. 3.

FIG. 5 is a partial diametral longitudinal cross-sectional view of a wheel sampling head.

Throughout the following description, like reference numerals are used to denote like parts of the drawings.

DETAILED DESCRIPTION OF THE PREFERRED EMBODIMENTS

The on-the-move ground sampling head designs described hereinafter all include a silicone membrane and a heating element. Variations in the design allow the head to be rolled or dragged behind a moving platform.

The present invention can be adapted to include a wheel, tubing or bar configuration with the basic concept remaining the same.

In the basic designs a piece of silicone is allowed to contact the ground. A heating element is placed next to the interior surface of the silicone element. An air gap is designed between the nearing element and the silicone element. The air gap is formed by voids around the heating element. In the tube design shown in FIG. 2 an inner core is used to fill up undesired voids thus decreasing the total volume of the air gap. A male electrical-pneumatic connector is used to pass electrical heating current from a transfer line to the sampling head. The connector is also used to pass air flow from the sampling head into a transfer line and thence to the mass spectrometer analyzer.

Referring now to FIG. 1 a modified transfer line, which is 3.5 meters in length, includes a center section standard GEMS transfer line 10 electrically and pneumatically connected to a standard GEMS connector 12 having its output end 14 coupled to a standard GEMS not shown. The input end of the modified transfer line includes a quick-connect female connector member 16. The on-the-move ground sampling heads shown in FIGS. 2, 3 and 5 attach to the transfer line 10 at the modified female connector member 16. The transfer line female input connector member 16 has been designed so that the aforementioned on-the-move sampling heads can be quickly removed and replaced. Air flow from the sampling heads enter the transfer line 10 via an axially disposed transfer tubing 18. The sampling heads are supplied with elecrical power via electrical jack terminals 20 and 22 which are insulated from each other by the female connector housing 16. Jacks 20 and 22 are connected to wires 21 and 23 respectively which are connected to a GEMS power supply not shown.

Referring now to the tube type sampling head of FIG. 2, a silicone membrane tube 24 fixedly supports an end Cap member 26 on one end and a male electrical-pneumatic plug connector 28 on its other end. The latter mates with the female connector 16 helically shaped heating coil 30 is operatively positioned inside of the tubular silicone membrane 24 by a nonconductive cylindrically shaded inner core member 32 and is of such size as to provide an annular air gad 34 which is pneumatically connected to an air interface port 36 which is in axial alignment with and slidably fits over the transfer tubing 18 of the female connector 16. The heater electrical connection ends 38 and 40 mate with the female jack connectors 20 and 22 respectively. The outer cylindrical surface 42 of the plug connector 28 slidably fits into the counter bore 44 of the female connector member 16 of FIG. 1.

Referring now to FIGS. 3 and 4 the bar type sampling head has a lower flat silicone membrane 46 and a flexible flat top surface 48 which sandwiches therebetween a planar shaped heating element 50. Heating element 50 has air gaps 52 which are pneumatically connected to air interface port 36 axially located in a quick-connect female connector 16 of the same configuration as that aforedescribed in FIG. 2. The heating element 50 also has electrical plug connections 38 and 40 as aforedescribed in FIG. 2.

Referring now to FIG. 5, the sampling head configuration has a silicone membrane element formed in the shape of a tire 54. Tire membrane 54 is supported by outer rim members 56, 56' which are fixedly attached to a hub member 58. Inner rim members 60, 60' are also operatively fixed to hub 58 and in abutment with outer rims 56, 56'. An air gap 62 is developed by the difference in the diameters between the outer rim 56, 56' and inner rim members 60, 60'. Radial air channels 64 is perpendicular to the axis of the wheel and allow air to travel from the outside air gaps 62 to the center of the wheel. The tire/rim assembly mounts onto the free spinning hub member 58. A zig zag heating element 66 is mounted within the air gap 62. The power leads 68 to the heater 66 are channeled toward the center of the wheel. The hub 58 allows the wheel to spin, provides a means for channel air from the wheel to be connected to a support boom 70. Hub 58 also provides a means to carry the electrical current to the heating element 66. The support boom 70 provides Support to the tire rim assembly, a boom air channel 72 to channel the air flow and electrical conductors 74 and 76 to carry current from the wheel into the modified transfer line shown in FIG. 1 via the plug connector 42.

In operation the on-the-move ground sampling heads shown in FIGS. 2, 3 or 5 are dragged or rolled by a NBC Reconnaissance System. The silicone membrane is continuously exposed to all the contaminants/chemicals on the road or terrain. Metal braiding or metal strips, not shown, are added to the exposed silicone membrane surface to limit the silicone abrasion during on-the-move operations. Should the silicone membrane encounter contaminating agents, a portion of this material would permeate into the membrane. The contaminant would penetrate the membrane and would be distributed throughout it. Some of the contaminant would then permeate into the interior air gads of the sampling head. This process is controlled by the requirement of matter or reach a state of thermodynamic equilibrium. These vapors are then drawn into the modified transfer line of FIG. 1 and to the GEMS where the final analysis is accomplished. The heating of the silicone membrane serves two functions. First, it increases the rate of transport of the contaminating agent across the silicone membrane. It also aids in cleaning the silicone membrane. Second, the heat limits any absorption onto the sampling head interior surfaces.

The present on-the-move ground sampling heads can be easily and rapidly replaced should they become damaged or contaminated. The quick change is accomplished by the quick-connects plug and jack connector members 16 and 42 aforedescribed.

While specific embodiments of the invention have been shown and described in detail to illustrate the application of the principles of the invention, it will be understood that the invention may be embodied otherwise without departing from such principles.

What is claimed is:

1. An on-the-move direct-contact surface sampling head for use with a gas analyzer such as a mass spectrometer or the like which comprises:

a transfer line having an output end connector for connection to a gas analyzer, an input end connector, a plurality of electrical power wires extending between and terminating at said input end connector and said output end connector, and a hollow transfer tubing extending between and terminating at said input end connector and said output end connector; and sampling head means detachably connected to the input end connector of said transfer line for contacting surfaces to be examined from a moving platform to determine existence of chemical contaminants, said sampling head means including a permeable membrane member having an outer surface for contacting the surface to be examined and having an other surface, means enclosing said other surface to form an interior chamber therewith, said means enclosing said other surface including a sampling head connector configured for mating engagement with said output end connector of said transfer line, heating means disposed within said interior chamber for heating said other surface and having electrical connection ends terminating in said sampling head connector for mating engagement with said electrical power wires of said transfer line, and air port means extending through said sampling head connector into communication with said interior chamber and positioned for mating engagement with said hollow transfer tubing of said transfer line.

2. An on-the-move surface sampling head as recited in claim 1 wherein:

said permeable membrane member is a tubular shaped membrane having opposed open ends and having said other surface as an interior wall thereof;

said means enclosing said other surface includes an end cap which seals one end of said tubular shaped membrane;

said sampling head connector is fixedly positioned in the other end of said tubular shaped membrane;

a non-conductive inner core member disposed in said tubular shaped membrane leaving an air gap between said other surface and the exterior surface of said cylindrical inner core member; and said heating means is an electrical heating element disposed intermediate said other surface and said inner core member.

3. An on-the-move surface sampling head as recited in claim 2 wherein said inner core member has a cylindrical shape and is disposed substantially concentric with said other surface of said tubular shaped membrane such that said air gap is substantially uniform throughout its extent.

4. An on-the-move surface sampling head as recited in claim 2 wherein said inner core member fills a substantial portion of said interior chamber to significantly reduce the volume of the air gap and thereby enhance sensitivity of said sampling head means to the presence of chemical contaminants.

5. An on-the-move surface sampling head as recited in claim 1 wherein:

said permeable membrane member is a bar shaped membrane;

said means enclosing said other surface includes a flat top surface member spaced above said bar shaped membrane such that said interior chamber has a substantially planar shape;

said heating means is a planar shaped heating element disposed intermediate and substantially parallel to said bar shaped membrane and said top surface member to provide a substantially planar air gap therebetween; and said sampling head connector is operatively attached to said bar shaped membrane and said top surface member.

6. An on-the-move surface sampling head as recited in claim 5 wherein said flat top surface member is flexible.

7. An on-the-move surface sampling head as recited in claim 5 wherein said permeable membrane member is a sheet of silicone.

8. An on-the-move surface sampling head as recited in claim 1 wherein:

said permeable membrane member is a tire shaped membrane having said other surface as an interior wall thereof;

said means for enclosing said other surface includes wheel means for supporting said tire shaped membrane and said heating means, hub means connected to said wheel means for allowing said wheel means to be free running, boom means having opposed ends, one end being connected to and supporting said hub means, said wheel means, hub means and boom means including means for providing an electrical connection therethrough to said heating means and means for providing a pneumatic connection therethrough to said interior chamber; and said sampling head connector is attached to the other end of said boom means and is in electrical and pneumatic communication with said means for providing an electrical connection and said means for providing a pneumatic connection.

9. An on-the-move surface sampling head as recited in claim 8 wherein said heating means includes:

a zig zag shaped heater element operatively disposed against said other surface of said tire shaped membrane.

10. An on-the-move surface sampling head as recited in claim 9 wherein said wheel means includes:

a pair of outer rim members supported by said hub means; and a pair of inner rim members supported by said hub means and located between said outer rim members and separated therefrom, said inner rim members being of smaller diameter than said outer rim members thereby producing an air gap between the inside surface of said tire shaped membrane and the outside circumference of said inner rim member, and creating a radially disposed air channel which pneumatically communicates with said air gap.

11. An on-the-move surface sampling head as recited in claim 1 wherein said permeable membrane member is a silicone membrane.

12. An on-the-move surface sampling head as recited in claim 1 wherein;

said permeable membrane member has a flat sheet configuration; and said means enclosing said other surface to form an interior chamber therewith includes a top surface member having a flat configuration on an underside surface thereof and being juxtaposed over said permeable membrane member to form a substantially planar interior chamber.

13. An on-the-move surface sampling head as recited in claim 12 wherein; said top surface member is flexible.

14. An on-the-move surface sampling head as recited in claim 13 wherein; said permeable membrane member is a sheet of silicone.

15. An on-the-move surface sampling head as recited in claim 1 wherein said heater means abuts portions of said other surface of said permeable membrane member to enhance vaporization of chemical contaminants which have permeated through said permeable membrane member to said other surface.

16. An on-the-move surface sampling head as recited in claim 1 wherein said permeable membrane member is a tubular shaped silicone membrane.

* * * * *